US010640824B1

(12) United States Patent
Peikon et al.

(10) Patent No.: US 10,640,824 B1
(45) Date of Patent: May 5, 2020

(54) METHODS OF IDENTIFYING NUCLEIC ACIDS FROM A SINGLE CELL USING AN ELECTRICAL CELL-TRAPPING ARRAY

(71) Applicant: Verily Life Sciences LLC, Mountain View, CA (US)

(72) Inventors: Ian Peikon, Bethpage, NY (US); Andrew Homyk, Belmont, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 416 days.

(21) Appl. No.: 15/608,364

(22) Filed: May 30, 2017

Related U.S. Application Data

(60) Provisional application No. 62/345,477, filed on Jun. 3, 2016, provisional application No. 62/348,223, filed on Jun. 10, 2016.

(51) Int. Cl.
| | | |
|---|---|---|
| *C12Q 1/6874* | (2018.01) | |
| *C12Q 1/6837* | (2018.01) | |
| *C12Q 1/6806* | (2018.01) | |
| *G01N 27/447* | (2006.01) | |

(52) U.S. Cl.
CPC ......... *C12Q 1/6874* (2013.01); *C12Q 1/6806* (2013.01); *C12Q 1/6837* (2013.01); *G01N 27/44791* (2013.01)

(58) Field of Classification Search
CPC .................................................... C12Q 1/6874
USPC ............................................................ 506/3
See application file for complete search history.

(56) References Cited

U.S. PATENT DOCUMENTS

| | | | |
|---|---|---|---|
| 2015/0009966 A1 | 1/2015 | Ariyavisitakul et al. | |
| 2015/0219618 A1* | 8/2015 | Krishnan | ................ B03C 5/005 |
| | | | 506/3 |

FOREIGN PATENT DOCUMENTS

| | | | | |
|---|---|---|---|---|
| WO | WO-2009146143 A2 * | 12/2009 | ........... | G01N 27/447 |
| WO | WO-2015031691 A1 * | 3/2015 | | |

OTHER PUBLICATIONS

Tuukkanen et al. (Nano Letters, 6, 2006, pp. 1339-1343) (Year: 2006).*
Kosuri et al., "Large-scale de novo DNA synthesis: technologies and applications", Nature methods 11.5 (2014): 499-507.
Morimoto et al., "High-density dielectrophoretic microwell array for detection, capture, and single-cell analysis of rare tumor cells in peripheral blood", PloS one 10.6 (2015): e0130418.

* cited by examiner

*Primary Examiner* — Karla A Dines
(74) *Attorney, Agent, or Firm* — Kilpatrick Townsend & Stockton LLP

(57) ABSTRACT

Provided herein are methods, systems, kits and compositions for identifying nucleic acids of interest from individual cells. The methods include isolating single cells on electrodes and identifying nucleic acids of interest from the isolated cells by sequencing.

22 Claims, 2 Drawing Sheets

US 10,640,824 B1

METHODS OF IDENTIFYING NUCLEIC ACIDS FROM A SINGLE CELL USING AN ELECTRICAL CELL-TRAPPING ARRAY

CROSS-REFERENCES TO RELATED APPLICATIONS

This application claims priority to U.S. Provisional Application No. 62/345,477, filed Jun. 3, 2016 and U.S. Provisional Application No. 62/348,223, filed Jun. 10, 2016, which are incorporated by reference herein in their entireties.

BACKGROUND

Heterogeneity is a ubiquitous feature of biological systems, and a complete understanding of such systems requires a method for uniquely identifying and characterizing individual cells and the nucleic acids within each cell. Current methods and devices for high throughput sequencing of nucleic acids with single-cell resolution include devices based on droplet microfluidic platforms. Electrode arrays are used for the deposition of DNA oligonucleotides of defined sequence and position (Kosuri and Church, Nature Methods 11(5):499-507 (2014)). Cell capture arrays using dielectrophoresis are known such as the detection of circulating tumor cells from patient blood samples (Morimoto et al., PloS One 10(6) (2015)). However, these methods do not allow for a low cost, efficient method of characterizing individual cells and identifying nucleic acids from individual cells.

BRIEF SUMMARY

Provided herein are methods of identifying nucleic acids of interest within single cells. The methods include contacting a solid surface with a plurality of cells wherein the solid surface comprises an array of identical features, wherein each identical feature comprises a library of distinct oligonucleotides, wherein each oligonucleotide comprises at least one unique molecular identifier sequence and a sequence complimentary to one of a plurality of nucleic acids of interest, immobilizing single cells at the identical features on the array on the solid surface by application of an electric field, releasing the nucleic acids of interest from the cells, hybridizing the oligonucleotides to the nucleic acids of interest, sequencing the released hybridized nucleic acids of interest and oligonucleotides to generate sequence data, and analyzing the sequence data to identify nucleic acids of interest within the single cells. Also provided are compositions, systems, and kits for identifying nucleic acids of interest within single cells.

BRIEF DESCRIPTION OF THE DRAWINGS

These and other features, aspects, and advantages of the present application will become better understood with regard to the following description and accompanying drawings.

DETAILED DESCRIPTION

The provided methods, systems, kits and compositions can be used for high-throughput nucleic acid, e.g., DNA or RNA, sequencing with single cell resolution. The provided methods, kits and compositions provide for high-throughput, low cost, high-capture efficiency for identification of nucleic acid sequences of single cells.

Provided are methods, systems, kits and compositions for analyzing with single cell resolution all or part of the nucleic acid molecules present within the cell. Thus, analysis of all or part of a transcriptome, or all or part of a genome or exome with single cell resolution can be carried out as described herein. The methods, systems, kits and compositions take advantage of an electric field to localize cells or their nucleic acid contents to a particular location on a surface. Optionally, the surface is configured such that a library of oligonucleotides having sequences complementary to all or a portion of a plurality of nucleic acids of interest (whose presence and/or amount in a cell is to be interrogated) is bound to a feature on the surface.

Optionally, the oligonucleotides include a barcode that identifies the location of the oligonucleotide on the surface, which serves as a proxy for a single cell. Optionally, all oligonucleotides from a single location (or feature) include identical location barcodes. Optionally, the oligonucleotides also include a unique molecular identifier sequence, which is unique to an individual capture oligonucleotide molecule. Optionally, the oligonucleotides further include a sequencing adaptor. Optionally, the configuration of the oligonucleotides are as set forth in FIG. 1, although as will be recognized by a person of ordinary skill, some variation in the order of the barcode and the unique molecular identifier sequence is within the scope of the present application.

Figure 2:
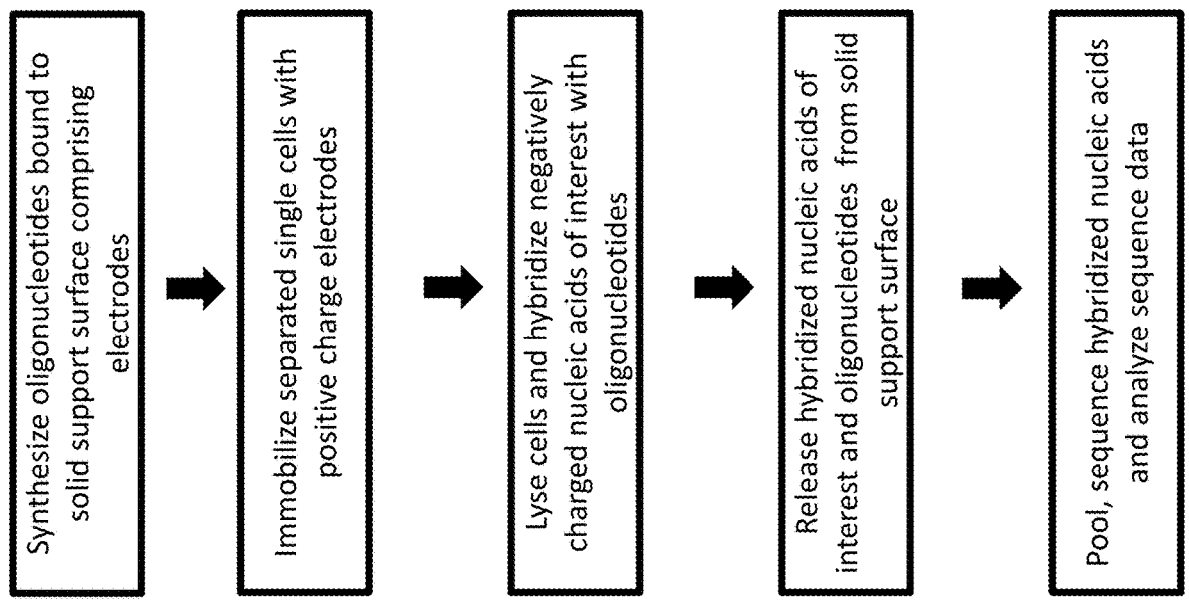
FIG. 2 is a schematic showing a flow diagram of the steps for performing an embodiment of the provided methods. Oligonucleotides are synthesized and immobilized on a solid surface comprising electrodes. Individual cells are separated and immobilized on an electrode. The cells are lysed and the cell's nucleic acids (comprising the nucleic acids of interest) are hybridized to the immobilized oligonucleotides. The hybridized nucleic acids of interest and oligonucleotides are released from the solid surface. Finally, the released nucleic acids are pooled and sequenced.

The provided methods can be carried out according to the flow chart set out in FIG. 2. The solid surface can comprise an array of electrodes that can be energized by a power supply to generate an electric field that is used to immobilize or help immobilize cells that are flowed over or otherwise are brought into contact with the surface of the array. Optionally, the methods are carried out at or above neutral pH such that under the influence of the electric field, cells and nucleic acids migrate toward the anode.

Disclosed herein are compositions and methods useful for the identification of nucleic acids of interest within single cells. The methods include immobilizing single cells at distinct locations on a solid surface using an electric field, wherein the solid surface comprises an array of identical features, wherein each identical feature comprises a library of distinct oligonucleotides and wherein the oligonucleotides comprise a unique molecular identifier sequence and a sequence complimentary to a nucleic acid of interest. Optionally, a single cell is immobilized at the identical feature. Once the cells are immobilized the nucleic acids can be released from the cells and hybridized to the oligonucleotides on the solid surface. The hybridized oligonucleotides and nucleic acids of interest can be sequenced to associate the nucleic acids of interest with a single cell. Accordingly, the provided methods can include analyzing the sequence data to identify nucleic acids of interest within the single cells. Optionally, analyzing the sequence data comprises quantifying the identified nucleic acids of interest using the unique molecular identifier sequence. Optionally, analyzing comprises sorting the read lengths of the data obtained from the sequencing step and identifying sequences of nucleic acids of interest present in read lengths exceeding a predetermined threshold. Optionally, the predetermined threshold is the maximum length of the distinct oligonucleotides. Optionally, the array comprises at least 10, 100, 1,000, 10,000, 100,000, 200,000, 300,000, 400,000, 500,000, 600, 00, 700,000, 800,000, 900,000, 1,000,000, or 10,000,000 identical features. Optionally, the solid surface comprises a plurality of electrodes each individually associated with an identical feature. Optionally, each electrode has a diameter of less than 2 microns. Optionally, each electrode binds to a single cell.

As used herein, the terms "nucleic acids of interest" or "nucleic acid sequences of interest" refer to a polynucleotide sequence to be analyzed, interrogated (e.g., sequenced) or quantitated. Typically, many different nucleic acid sequences of interest are simultaneously analyzed, interrogated or quantitated from a single sample. Nucleic acid sequences of interest include, but are not limited to, RNA, coding regions, intron regions, genes, exons, cDNA, promoters, enhancers, or fragments thereof of interest.

As used herein, electrode array or an array of electrodes refers to a solid surface comprising a plurality of cathode electrodes, anode electrodes or a combination thereof.

As used herein, an array of identical features refers to a plurality of known locations on the solid surface each known location being an identical feature. The identical feature can include one or more oligonucleotides, one or more electrodes or any combination thereof. Optionally, the identical feature comprises an electrode and a plurality of oligonucleotides. Optionally, the identical feature comprises at least two electrodes and a plurality of oligonucleotides. Optionally, the identical feature comprises a plurality of oligonucleotides and at least one electrode at or near the site of the identical feature.

The terms cell capture and cell trapping refer to movement of cells in an electrical current through electrophoresis or dielectrophoresis and immobilizing cells through electrical charge interactions between cells and charged surfaces.

As used herein, barcode refers to a sequence that can be used to identify a specific oligonucleotide through analysis of sequencing data. For example, the barcode can identify the location to which the oligonucleotide is bound on a solid surface. Optionally, the barcode is the same for each oligonucleotide located at an identical feature on the solid surface. Barcodes can range in size, for example, each barcode can be about 3 to 30 nucleotides in length. Thus, a barcode can be 3, 4, 5, 6, 7, 8, 9, 10, 11, 12, 13, 14, 15, 20, 25, 30 or more nucleotides in length.

The term unique molecular identifier or unique molecular identifier sequence refers to a sequence synthesized using random addition of mixed bases during synthesis to produce a sequence that can be used to identify a specific oligonucleotide molecule through analysis of sequencing data. Unique molecular identifier can range in size, for example, each unique molecular identifier can be about 3 to 30 nucleotides in length. Thus, a unique molecular identifier can be 3, 4, 5, 6, 7, 8, 9, 10, 11, 12, 13, 14, 15, 20, 25, 30 or more nucleotides in length. Optionally, the unique molecular identifier sequence between 5 and 30 bases in length.

Optionally, the oligonucleotides are bound directly to electrodes on the surface. Optionally, the oligonucleotides are conjugated to the electrodes. Optionally, the library of oligonucleotides include within a single location or feature on the surface, multiple oligonucleotides that include sequences complementary to the same nucleic acid of interest. Those complementary sequences can be identical or they can be directed to different regions of the nucleic acid of interest. Optionally, the library of oligonucleotides include within a single location or feature on the surface, multiple oligonucleotides that include sequences complementary to different nucleic acids of interest. The presence of multiple oligonucleotides enables quantitation of the nucleic acids of interest through analysis of sequence read information. The presence of the unique molecular identifier sequence controls for bias in amplification and/or sequencing.

The disclosed oligonucleotides can further include a sequencing adapter sequence and a first barcode sequence corresponding to the location of the identical feature on the array. Optionally, the disclosed oligonucleotides include a second barcode sequence corresponding to the identity of a predetermined nucleic acid sequence of interest. Optionally, the second barcode is associated with a genomic location, a transcript identity or a predetermined nucleotide sequence. Optionally, the first barcode or the second barcode is synthesized through controlled addition of mixed nucleotides. Optionally, the synthesis by controlled addition of mixed nucleotides is performed by electrochemical detritylation. Optionally, the synthesis by controlled addition of mixed nucleotide bases employs an electrode. The oligonucleotides can be synthesized using a semiconductor (Kosuri and Church, et al., PloS One 10(6) (2014)). The oligonucleotides can also be synthesized using electrochemistry or photoelectrochemistry. The oligonucleotide synthesis can also comprise detritylation. One example of a method for oligonucleotide synthesis comprises light to gate the electrochemical generation of protons at a semiconductor anode that is addressed by a digital micro-mirror device. These protons then cleave the acid-labile dimethoxytrityl protecting groups of standard phosphoraidite reagents at the virtual electrode.

Oligonucleotides can be attached to the solid support surface by any number of methods that is known in the art such as, covalent attachment of the oligonucleotide to the solid support, such as using a primary amine to the 5' or 3' terminus of the oligonucleotide or an internal amino modified base, such as amino-deoxy cytosine or amino-deoxy thymine. The oligonucleotide may also be attached to the solid support using a thiol modified nucleotide base at the 5' or 3' terminus or an internal nucleotide base. The thiol modified nucleotide can be used to form a reversible disulfide bond or irreversible bonds with a variety of activated accepting groups on the solid support surface. For example, incorporation of a thiol group at the 5' end of an oligonucleotide may be achieved with S-tryityl-6-mercaptohexyl derivatives.

Figure 1:
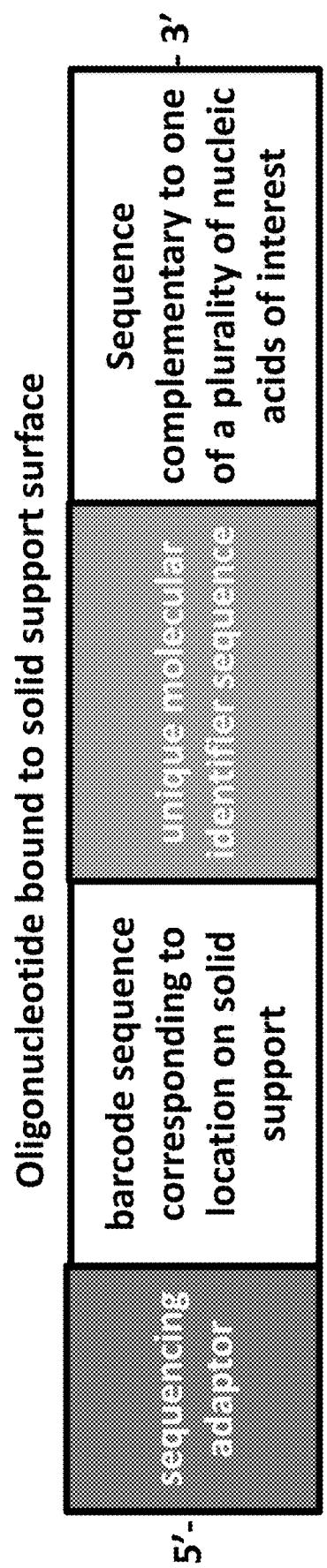
FIG. 1 is a schematic showing an exemplary oligonucleotide bound to a solid surface. The exemplary oligonucleotide comprises from 5' to 3' a sequencing adaptor, a barcode sequence, a unique molecular identifier, and a sequence complementary to a nucleic acid of interest.

Optionally, at each electrode position a library of oligonucleotides is synthesized. Optionally, 10,000 to 100,000 distinct oligonucleotides are present at each feature and associated with an individual electrode. Optionally, a library of 1-100, 100-1,000, 1,000-10,000 or 10,000-100,000, 100, 000-1,000,000 or more oligonucleotides is located at each feature with each library associated with an individual electrode. Each oligonucleotide can include, from 5' to 3', a sequencing adapter sequence, a barcode corresponding to the location of the oligonucleotide and, thus, the feature on the solid surface, a unique molecular identifier sequence and a nucleic acid targeting sequence complimentary to a nucleic acid of interest (FIG. 1). Optionally, for the capture of mRNA, the nucleic acid targeting sequence can be a homopolymer of thymine comprising 5-200 consecutive thymine bases. Optionally, the nucleic acid complimentary to a nucleic acid of interest is produced by using mixed nucleotides, wherein nucleotides are incorporated to specifically capture certain nucleic acids (i.e., for targeted capture of certain mRNA transcripts). Thus, each oligonucleotide on the surface has a known barcode corresponding to the position on the surface, and this barcode also serves as the cellular identifying barcode. Within a pool of barcode sequences in the same position (and bearing the same cellular barcode sequence), each oligonucleotide can include a unique random sequence (the unique molecular identifier sequence) based on synthesis using mixed bases.

Cells can be moved to the distinct locations, e.g., the identical features, on the solid surface using the electrode array. Optionally, the identical feature is configured to contain a single cell. For example, the identical feature can be a well or structure configured to contain a single cell. Optionally, the cells are moved by electrophoresis or dielectrophoresis. Optionally, the dielectrophoresis is performed by a planar electrode of negative charge placed over the solid support surface with an electrolyte solution placed between the planar electrode of negative charge and the solid surface. Optionally, the solid surface comprises an electrode of positive charge. Optionally, the individual electrodes are independently controlled, allowing selective capture and/or release of cells. Optionally, the electrodes may capture cells of interest in the vicinity of the electrode. Optionally, the cells are moved to the distinct locations on the solid support surface by electrophoresis.

By way of example, the electrodes can be used to electrophoretically transport cells from one position to another through dielectrophoresis, optionally, with the use of visual feedback from the cameras integrated with microscopes. Dielectrophoresis is performed by application of an alternating current (AC) electric field across the electrode array. Sinusoidal voltages of frequencies in the range of 200 kHz to 10 MHz can be used and voltages in the range of 4 to 10 V in magnitude can be used for dielectrophoresis. For example, electrodes placed every 1-2 µm can be used to capture cells every 10-20 µm by using alternating current and the electrodes to guide cells into their final positions. Alternatively, electrophoresis using a direct current (DC) electric field can be used to electrophoretically transport cells from one position to another. Optionally, cell populations of various cell numbers are used and may be similar in number, less than or exceeding the number of electrodes present on the electrode array.

Cell populations of 10-100, 100-1,000, 1,000-10,000, 10,000-100,000, 100,000-200,000, 200,000-300,000, 300,000-400,000, 400,000-500,000, 500,000-600,00, 600,000-700,000, 700,000-800,000, 800,000-900,000, 900,000-1,000,000, or 1,000,000-10,000,000 cells can be used. Additionally, the electrode array can have 10-100, 100-1,000, 1,000-10,000, 10,000-100,000, 100,000-200,000, 200,000-300,000, 300,000-400,000, 400,000-500,000, 500,000-600,00, 600,000-700,000, 700,000-800,000, 800,000-900,000, 900,000-1,000,000, or 1,000,000-10,000,000 electrodes. Any cell type can be used, such as, but not limited to human, mammalian, yeast or bacterial cells. Optionally, a cell population of 100,000 cells is applied to the solid support surface comprising 1,000 electrodes.

After immobilization of cells, optionally, the solid surface can be washed one or more times with a suitable solution. Optionally, the solid surface is washed with 0.5 L of phosphate buffered saline, or other physiological buffer, 1, 2, 3, 4, 5 or more times. Alternatively, the solid support surface can be washed with a volume of 100 mL to 10 L of any compatible solution for any number of times sufficient to remove unbound cells and maintain bound cells on the electrode surfaces.

Cells can be lysed using a standard buffer comprising sodium dodecyl sulfate. Alternatively, cells may be lysed by a variety of means including: application of heat, electroporation (passing high voltage through the electrodes) or chemical methods, such as washing the solid support with a solution comprising detergents such as, but are not limited to, Triton X-100 or Sodium dodecyl sulfate. Solutions used for lysis include, but not limited to, solutions buffered with salts (e.g., Tris-HCl or EDTA). Lysis causes the release of the nucleic acids of interest, which are captured or immobilized via hybridization with the sequence complementary to the nucleic acid of interest present on the oligonucleotides on the array. Optionally, the nucleic acids of interest are released by electroporation. Released nucleic acids of interest can be guided to the oligonucleotides by performing electrophoresis using the electrodes.

Once the nucleic acids of interest are released from the cells, capture efficiency of the nucleic acids released from the cells can be increased by maintaining pH conditions such that released nucleic acids are negatively charged and migrate toward an anode to bind to the barcoded oligonucleotides. In another example, the released nucleic acid molecules are captured by performing electrophoresis using the electrode to guide the released nucleic acid to the oligonucleotides on the solid surface.

Once nucleic acids of interest have been hybridized to the oligonucleotides, the solid surface may again be washed one or more times to remove any unbound nucleic acids. After washing, the hybridized molecules can be separated from the solid surface by a variety of means taking advantage of the linkage chemistry used to initially attach the oligonucleotide to the solid surface.

Once hybridized molecules are separated from the solid surface, the nucleic acids of interest bound to the barcoded oligonucleotides can be pooled in a single tube, processed, amplified and sequenced (FIG. 2). mRNA transcripts hybridized to the oligonucleotides comprising homopolymer thymine or sequences complimentary to specific mRNA transcripts of interest are reverse transcribed to cDNA by conventional methods using reverse transcriptase. The pooled, extended and reverse transcribed oligonucleotides are then amplified and sequenced by high throughput sequencing methods. Other nucleic acids of interest can also be amplified and sequenced by high throughput sequencing such as, but not limited to, genomic DNA or non-coding RNA (RNA molecules that do not encode a protein). By way of example, Illumina® sequencing primers can be used to first amplify the cDNA by annealing to the sequencing adapter sequences present on the oligonucleotide at the 5' end of the oligonucleotide (FIG. 1).

The term sequencing refers to all methods related to sequencing nucleic acid, including, high throughput sequencing. The term high throughput sequencing refers to all methods related to sequencing nucleic acid where more than one nucleic acid sequence is sequenced at a given time. Sequencing methods include, but are not limited to, sequencing-by-synthesis, Sanger or gel-based sequencing, sequencing-by-hybridization, sequencing-by-ligation, Maxam-Gilbert sequencing, chain-termination, de Novo sequencing, shot gun sequencing, and next generation sequencing methods, including quantitative massively parallel sequencing, Polony sequencing, 454 pyrosequencing, Supported Oligo Ligation Detection sequencing, Ion Torrent® semiconductor sequencing (Life Technologies, Carlsbad, Calif.), DNA nanoball sequencing, Nanopore® DNA sequencing (Oxford Nanopore Technologies, Oxford, UK), Tunnelling currents DNA sequencing, sequencing with mass spectrometry, microfluidic Sanger sequencing, RNAP sequencing or any other available sequencing method. Thus, the sequencing is carried out by a variety of known methods, including, but not limited to, sequencing by ligation, sequencing by synthesis or sequencing by hybridization, which are well known in the art, and familiarity by the reader with such methods is assumed. See, for illustration and not limitation, Shendure, J. and H. Ji. "Next-generation DNA sequencing," Nature biotechnology 26.10 (2008): 1135-1145; Shendure, J., et al. "Advanced sequencing technologies: methods and goals" Nat. Rev. Genet. 5, 335-344 (2004); Metzker, Michael L. "Sequencing technologies—the next generation," Nature Reviews Genetics 11.1 (2010): 31-46; Drmanac, R. et al. "Accurate Whole Genome Sequencing as the Ultimate Genetic Test," Clinical Chemistry 61.1 (2015): 305-306; Drmanac, R. et al. "Human genome sequencing using unchained base reads on self-assembling DNA nanoarrays," Science 327.5961 (2010): 78-81; Drmanac, S. et al. "Accurate sequencing by hybridization for DNA diagnostics and individual genomics," Nat. Biotechnol. 16, 54-58 (1998); Margulies, M. et al. "Genome sequencing in microfabricated high-density picolitre reactors," Nature 437.7057 (2005): 376-380; Ng, S. et al. "Targeted capture and massively parallel sequencing of 12 human exomes," Nature 461.7261 (2009): 272-276; Meng, H-M et al. "DNA dendrimer: an efficient nanocarrier of functional nucleic acids for intracellular molecular sensing," ACS Nano 8.6 (2014): 6171-6181; Shendure, J. et al. "Accurate multiplex polony sequencing of an evolved bacterial genome," Science 309, 1728-1732 (2005); Brenner, S. et al. "Gene expression analysis by massively parallel signature sequencing (MPSS) on microbead arrays" Nat. Biotechnol. 18, 630-634 (2000); Ronaghi et al. "Real-time DNA sequencing using detection of pyrophosphate release" Anal. Biochem. 242, 84-89 (1996); McKernan, K. et al. "Reagents, methods, and libraries for bead-based sequencing," U.S. Patent Application Publication No. 2008/0003571 (2006); Adessi, C. et al. "Solid phase DNA amplification: characterisation of primer attachment and amplification mechanisms" Nucleic Acids Res. 28, e87 (2000), each of which is incorporated in its entirely for all purposes, including for teaching preparation of DNA sequencing libraries and MPS sequencing platforms and techniques.

The sequence data obtained using the provided methods can be analyzed to assign the nucleic acid of interest to a single cell. Optionally, assigning the nucleic acid of interest to a single cell comprises identifying in the sequence data the presence of the common sequence corresponding to the location of the solid surface to which the cell was localized. The sequencing data is analyzed. In exemplary embodiments, read lengths shorter than a predetermined threshold are discarded. The predetermined threshold can be the length of the capture oligonucleotides attached to the solid support surface. The predetermined threshold can be shorter than the length of the oligonucleotides attached to the solid support surface. Alternatively, the predetermined threshold may be longer than the length of the oligonucleotides attached to the solid support surface, but shorter than the average read length of the run sequences.

The sequence data can be further analyzed by using the unique molecular identifier sequence to assign each unique molecular identifier sequence to each original hybridized oligonucleotide, thereby eliminating amplification bias. The barcode sequence corresponding to the location of the array feature on the solid support surface can be used to assign the read sequence to a single cell of origin. The abundance of sequences corresponding to an individual nucleic acid of interest from a single cell is used to quantitate the abundance of the nucleic acid in the single cell. Accordingly, the abundance of sequences corresponding to individual mRNA sequences from a single cell is used to quantitate the relative level of gene expression of genes of interest in each single cell.

Also provided are solid surfaces comprising a plurality of electrodes and an array of identical features, wherein each identical feature comprises a library of distinct oligonucleotides wherein each oligonucleotide includes i) a sequencing adaptor sequence; ii) a barcode sequence corresponding to the location of the identical feature on the array on the solid surface; iii) a unique molecular identifier sequence; and iv) a sequence complimentary to one of a plurality of nucleic acids of interest. Optionally, the solid surface comprises more than one electrode at each identical feature. Optionally, the electrode has a diameter less than 2 microns. Optionally, the electrodes have a diameter greater than 2 microns. Optionally, a planar electrode of negative charge is combined with the solid surface. Optionally, the planar electrode of negative charge is positioned over the solid surface with space in between the solid surface and planar electrode of negative charge.

A surface or support for use in the provided methods described herein refers to any surface or collection of surfaces to which nucleic acids can be attached. Suitable surfaces include, but are not limited to, beads, resins, gels, wells, columns, chips, flowcells, membranes, matrices, plates or filters. For example, the surface can be latex or dextran beads, polystyrene or polypropylene surfaces, polyacrylamide gels, gold surfaces, glass surfaces, optical fibers, or silicon wafers. The surface can be any material that amenable to chemical modification to afford covalent linkage to a nucleic acid. Thus, the solid surface can be glass, porous glass, plastic, metal, silicon or any combination thereof. The solid support can be silver, copper, gold, aluminum, platinum, or another metallic electrical conduction surface, or any combination thereof. The solid support can comprise an additional layer of agarose, polyacrylamide, starch or another suitable porous material to permit migration of cells and provide appropriate electrical resistance.

Optionally, the solid surface comprises wells or structures for containing cells. Optionally, the well or structure is configured to contain a single cell. Optionally, the well or structure is the identical feature, wherein the identical feature is configured to contain a single cell. Optionally, the wells or structures are fabricated over the electrodes on the surface such that only a single cell can fit within the well or structure. Optionally the wells or structures have a diameter greater than 2 microns. Optionally, the wells or structures are less than 100 microns in diameter. Optionally, the electrodes have a diameter greater than 2 microns. In certain embodiments, each feature on the array has a diameter smaller than the diameter of an individual cell, e.g., less than 2 microns. In other embodiments, the electrode array comprises a well or structure for containing cells positioned at each electrode or connected to each electrode, wherein the wells or cell container structures are less than 100 microns in diameter and wherein the wells or cell container structures can contain an individual cell.

The electrodes on the solid surface can be used for, but not limited to, one or more of the following procedures. The electrodes can be used to control the assembly of barcode sequences, to trap single cells by electrophoresis or dielectrophoresis, to perform electroporation on the trapped cells to release nucleic acids of interest from the cells, and/or to attract/capture released nucleic acids of interest to the electrode and/or oligonucleotides. Optionally, the electrodes can be individually and independently controlled.

Also provided herein are systems comprising a solid surface comprising a plurality of electrodes and an array of identical features, wherein each identical feature comprises a library of distinct oligonucleotides wherein each oligonucleotide includes i) a sequencing adaptor sequence; ii) a barcode sequence corresponding to the location of the identical feature on the array on the solid surface; iii) a unique molecular identifier sequence; and iv) a sequence complimentary to one of a plurality of nucleic acids of interest. Optionally, the system comprises a solid surface integrated with a microscope. Optionally, the solid surface is connected to the microscope. Optionally, the cells on the solid surface are visualized by microscopy. Optionally, the visualization is used to select and/or characterize specific cells. Optionally, the image data from the visualization can be used to select and/or characterize cells based on characteristics such as, size, morphology, fluorescent signals and/or other features or signals. Optionally, the visualization is used to guide movement of cells to electrodes. Optionally, image data produced from the microscopy is matched to sequencing data obtained from corresponding cells.

Thus, for example, the system is optionally integrated with optics and software to operate in a closed-loop fashion. The electrode arrays can be integrated with optics by designing the electrode arrays to be compatible with advanced microscopy lenses. For example, the electrodes may be fabricated on cover slips for integration into existing microscopy setups. Visual feedback from the cameras integrated with microscopes can be used to track and guide the transport of cells from one position to another by dielectrophoresis or electrophoresis. For example, the visualization may be used to guide cells to unoccupied electrodes on the array. The visual feedback may be used to track cell origins (by placing incoming cells into known locations) as well as provide a means to sort cells in situ (using the visual feedback from the camera, cells could be characterized and/or selected or rejected based on morphology, size, fluorescence or other characteristics or signals). The electrodes can be independently controlled to allow selective capture/release of cells with particular characteristics. The visual feedback may also be used to record high resolution microscope images, for example, fluorescent excitation/emission combinations). In addition, the visual images can be correlated with sequencing data obtained from corresponding cells based on spatial locations identified from barcodes.

Also provided are kits for identifying nucleic acids of interest within single cells. The kits include instructions for use and solid surfaces comprising a plurality of electrodes and an array of identical features, wherein each identical feature comprises a library of distinct oligonucleotides wherein each oligonucleotide includes i) a sequencing adaptor sequence; ii) a barcode sequence corresponding to the location of the identical feature on the array on the solid surface; iii) a unique molecular identifier sequence; and iv) a sequence complimentary to one of a plurality of nucleic acids of interest. The kits may further include in the same or separate containers enzymes for performing the provided methods including, for example, polymerases, fluorescent nucleotides, nucleic acids, adapters, primers or other reagents necessary for sequencing and or amplification.

Disclosed are materials, compositions, and components that can be used for, can be used in conjunction with, can be used in preparation for, or are products of the disclosed methods, compositions, and kits. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

EXAMPLES

Below are examples for carrying out the provided methods. The examples are offered for illustrative purposes only, and are not intended to limit scope.

Example 1. Production of an Electrode Array Bound to Oligonucleotides with Barcode Sequences An array of identical features is produced by electrochemically-controlled synthesis of oligonucleotides on a solid surface comprising electrodes. At each electrode position on the solid surface, a pool of distinct oligonucleotides is synthesized or spotted. Each oligonucleotide includes, from 5' to 3', a sequencing adapter sequence, a barcode sequence corresponding to the location of the oligonucleotide on the solid surface, a unique molecular identifier sequence and a nucleic acid complimentary to a nucleic acid of interest (FIG. 1).

Example 2. Single Cell Trapping

After fabrication of the oligonucleotides on the solid surface, single cells are captured or immobilized at different positions or features on the positively charged surface (FIG. 2). A negative source planar electrode is placed over the surface in a "sandwich" configuration. In between the surface and the planar electrode, an electrolyte solution is added. A solution of cells is passed over the surface while electrodes are energized to create a field that drives the migration of individual cells to individual features. The cells are suspended in a solution that is buffered to maintain the exterior of the cells with a negative charge, and migration will occur toward an anode. Because of the cells' large size relative to the diameter of the electrode, a cell will sterically block the addition of a second cell thereby driving occupancy to near 100%, with each electrode trapping only a single cell. The solid support surface is then washed to remove unbound cells.

Example 3: Cell Lysis and Sequencing

Cells trapped on the surface are then lysed to release nucleic acids of interest (FIG. 2). The cells are lysed using a standard buffer comprising sodium dodecyl sulfate. The nucleic acids of interest are then hybridized to the oligonucleotides. After hybridization of the nucleic acids of interest to the oligonucleotides, the solid surface comprising the hybridized nucleic acids and oligonucleotides is washed with a wash buffer to extensively remove cellular debris and unhybridized nucleic acids. The wash buffer can be TE buffer comprising 10 mM Tris and 1 mM EDTA buffered at a pH between 6 and 8. The solid support surface is washed 3-5 times with 0.5 L of TE buffer. The hybridized nucleic acids of interest and oligonucleotides are then separated from the surface.

Nucleic acids bound to the barcoded oligonucleotides are pooled in a single tube, processed, amplified and sequenced (FIG. 2).

Example 5: Analysis of Sequencing Data

The sequencing data is analyzed. Read lengths shorter than a predetermined threshold are discarded. The unique molecular identifier sequence information is used to assign each unique molecular identifier sequence to each original hybridized oligonucleotide, thereby eliminating amplification bias. The barcode sequence corresponding to the location of the feature on the solid surface is used to assign the read sequence to a single cell of origin. Finally, the abundance of sequences corresponding to an individual nucleic acid of interest from a single cell is used to quantitate the abundance of the nucleic acid in the single cell.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

What is claimed is:

1. A method of identifying nucleic acids of interest within single cells, comprising:
   contacting a solid surface with a plurality of cells wherein the solid surface comprises an array of identical features, wherein each identical feature comprises a library of distinct oligonucleotides, wherein each oligonucleotide comprises at least one unique molecular identifier sequence and a sequence complimentary to one of a plurality of nucleic acids of interest, wherein the surface further comprises a planar electrode of negative charge and wherein the planar electrode is positioned over the solid surface with space between the solid surface and planar electrode of negative charge;
   immobilizing at least one of the cells at one of the identical features on the array on the solid surface by application of an electric field;
   releasing the nucleic acids of interest from the cells;
   hybridizing the oligonucleotides to the nucleic acids of interest;
   releasing the hybridized nucleic acids of interest and oligonucleotides from the solid surface;
   sequencing the released hybridized nucleic acids of interest and oligonucleotides to generate sequence data; and
   analyzing the sequence data to identify nucleic acids of interest within the single cells.

2. The method of claim 1, wherein analyzing comprises sorting the read lengths of the data obtained from the sequencing step and identifying sequences of nucleic acids of interest present in read lengths exceeding a predetermined threshold.

3. The method of claim 1, wherein analyzing comprises quantifying the nucleic acids of interest.

4. The method of claim 1, wherein each oligonucleotide further comprises:
   a sequencing adaptor sequence; and
   a barcode sequence corresponding to the location of the identical feature on the array on the solid surface.

5. The method of claim 1, wherein the array comprises at least 10, 100, 1,000, 10,000, 100,000, 200,000, 300,000, 400,000, 500,000, 600,00, 700,000, 800,000, 900,000, 1,000,000, or 10,000,000 identical features.

6. The method of claim 1, wherein analyzing the sequence data comprises assigning the nucleic acids of interest to a single cell.

7. The method of claim 6, wherein assigning the nucleic acid of interest to a single cell comprises identifying in the sequence data the presence of the common sequence corresponding to the location of identical feature on the array on the solid surface to which the cell was localized.

8. The method of claim 1, wherein the solid surface comprises a plurality of electrodes, wherein each electrode is individually associated with an identical feature on the array.

9. The method of claim 8, wherein each electrode has a diameter of less than 2 microns.

10. The method of claim 8, wherein each electrode has a diameter of less than 100 microns.

11. The method of claim 8, wherein each electrode binds to a single cell.

12. The method of claim 8, wherein the unique molecular identifier sequence is between 5 and 30 nucleotides in length.

13. The method of claim 1, wherein the cells on the solid support surface are visualized by microscopy.

14. The method of claim 13, wherein the visualization is used to guide movement of cells to electrodes.

15. The method of claim 13, wherein image data produced from the microscopy is matched to sequencing data obtained from corresponding cells.

16. The method of claim 1, wherein the cells are moved to the distinct locations on the solid support surface by electrophoresis.

17. The method of claim 1, wherein the identical feature is configured to contain a single cell.

18. A solid surface comprising a plurality of electrodes and an array of identical features, wherein each identical feature comprises a library of distinct oligonucleotides wherein each oligonucleotide comprises:
   i) a sequencing adaptor sequence;
   ii) a barcode sequence corresponding to the location of the identical feature on the array on the solid surface;
   iii) a unique molecular identifier sequence; and
   iv) a sequence complimentary to one of a plurality of nucleic acids of interest
   wherein the surface further comprises a planar electrode of negative charge and wherein the planar electrode is positioned over the solid surface with space between the solid surface and planar electrode of negative charge.

19. The solid support surface of claim 18, wherein each electrode in the plurality of electrodes is located at an identical feature on the array and the library of distinct oligonucleotides is bound to the electrode.

20. The solid support surface of claim 18, wherein each electrode has a diameter less than 2 microns.

21. The solid surface of claim 18, wherein each identical feature is configured to contain a single cell.

22. A kit comprising the solid surface of claim 18 and instructions for use.

\* \* \* \* \*